US012723233B2

(12) United States Patent
Tabatabaei-Zavareh et al.

(10) Patent No.: US 12,723,233 B2
(45) Date of Patent: Sep. 1, 2026

(54) MEDIA AND METHODS FOR DIFFERENTIATING NATURAL KILLER CELLS

(71) Applicant: STEMCELL Technologies Canada Inc., Vancouver (CA)

(72) Inventors: Nooshin Tabatabaei-Zavareh, Vancouver (CA); Albertus Wernerus Wognum, Vancouver (CA)

(73) Assignee: Stemcell Technologies Canada Inc., Vancouver (CA)

( * ) Notice: Subject to any disclaimer, the term of this patent is extended or adjusted under 35 U.S.C. 154(b) by 1013 days.

(21) Appl. No.: 17/416,200

(22) PCT Filed: Dec. 20, 2019

(86) PCT No.: PCT/CA2019/051875
§ 371 (c)(1),
(2) Date: Jun. 18, 2021

(87) PCT Pub. No.: WO2020/124256
PCT Pub. Date: Jun. 25, 2020

(65) Prior Publication Data

US 2022/0056412 A1 Feb. 24, 2022

Related U.S. Application Data

(60) Provisional application No. 62/783,341, filed on Dec. 21, 2018.

(51) Int. Cl.
*C12N 5/0783* (2010.01)
*A61K 40/15* (2025.01)
*A61K 40/42* (2025.01)

(52) U.S. Cl.
CPC ............ *C12N 5/0646* (2013.01); *A61K 40/15* (2025.01); *A61K 40/428* (2025.01); *A61K 2239/48* (2023.05); *C12N 2500/90* (2013.01); *C12N 2501/125* (2013.01); *C12N 2501/2302* (2013.01); *C12N 2501/2307* (2013.01); *C12N 2501/2312* (2013.01); *C12N 2501/2315* (2013.01); *C12N 2501/2321* (2013.01); *C12N 2501/26* (2013.01); *C12N 2501/38* (2013.01); *C12N 2502/14* (2013.01); *C12N 2506/11* (2013.01); *C12N 2506/45* (2013.01)

(58) Field of Classification Search
CPC .......................... C12N 5/0646; C12N 2500/90
See application file for complete search history.

(56) References Cited

U.S. PATENT DOCUMENTS 9,585,914 B2 * 3/2017 Dilber ..................... A61P 35/00
10,828,329 B2 * 11/2020 Laganière ............... A61P 43/00
11,702,635 B2 * 7/2023 Hernandez ........... C12N 5/0647 424/93.7
2015/0374754 A1 12/2015 Dilber et al.
2019/0209618 A1 * 7/2019 Hope ..................... A61K 35/28

FOREIGN PATENT DOCUMENTS

CA 2972662 A1 7/2016
WO WO-2016191879 A1 * 12/2016 ............ A61K 35/15
WO 2017/173551 A1 10/2017

OTHER PUBLICATIONS

Li et al, (Stem Cell Res. May 2017:21:32-39. doi: 10.1016/j.scr.2017.03.014. Epub Mar. 21, 2017 (Year: 2017).*
Tabatabaei-Zavareh et al. (Differentiation of hematopoietic stem and progenitor cells to NK cells in a stroma free, serum-free culture system. Journal of Immunology, May 1, 2018, vol. 200, issue 1, Supplement, abstract 103.4) (Year: 2018) (Year: 2018).*
Mesquitta et al. (Pyrimido-indole derivative, UM171 promotes differentiation and expansion of myeloid progenitors and NK cells from human pluripotent stem cells, Experimental Hematology, 64(22), Aug. 2018, (Year: 2018) (Year: 2018).*
Tabatabaei-Zavareh et al. (Differentiation of hematopoietic stem and progenitor cells to NK cells in a stroma free, serum-free culture system. Journal of Immunology, May 1, 2018, vol. 200, issue 1, Supplement, abstract 103.4) (Year: 2018).*
Mesquitta et al. (Pyrimidoindole derivative, UM171 promotes differentiation and expansion of myeloid progenitors and NK cells from human pluripotent stem cells, Experimental Hematology, 64(22), Aug. 2018) (Year: 2018).*
Mesquitta, WT. et al., Pyrimido-indole derivative, UM171 promotes differentiation and expansion of myeloid progenitors and NK cells from human pluripotent stem cells, Experimental Hematology, 64(22), Aug. 2018.
Mesquitta, W-T et al., Pyrimido-indole derivative, UM171 expands distinct types of myeloid and lymphoid progenitors from human pluripotent stem cells. Blood, Nov. 29, 2018, vol. 132, Supplement 1:3835 (abstract).
STEMCELL Technologies. Expansion and Differentiation of Hematopoietic Stem and Progenitor Cells into Natural Killer Cells Using StemSpan Medium and Supplements. Technical Bulletin, Document #DX22912, Version 1.0.01, Nov. 2019 [online] Retrieved from https://www.stemcell.com/expansion-and-differentiation-of-hematopoietic-stem-and-progenitor-cells-into-natural-killer-cells-using-stemspan-medium-and-supplements.html.
Tabatabaei-Zavareh, N. et al., Differentiation of hematopoietic stem and progenitor cells to NK cells in a stroma-free, serum-free culture system. Journal of Immunology, May 1, 2018, vol. 200, issue 1, Supplement, abstract 103.4.
Journal of Immunology, vol. 200, Issue Supplement 1, p. 103.4(May 1, 2018).
Science, vol. 345(6203), p. 1509-1512(Sep. 19, 2014.).

* cited by examiner

*Primary Examiner* — Christopher M Babic
*Assistant Examiner* — Joel D Levin
(74) *Attorney, Agent, or Firm* — SMART & BIGGAR LP; Micheline Gravelle

(57) ABSTRACT

Media and methods for differentiating NK progenitor cells into NK cells are disclosed. The NK differentiation media comprises a pyrimidoindole compound such as UM171 or UM729.

13 Claims, 15 Drawing Sheets

A)

B)

A)

B)

A)

B)

A)

B)

C)

A)

B)

C)

D)

E)

A)

B)

C)

A)

B)

MEDIA AND METHODS FOR DIFFERENTIATING NATURAL KILLER CELLS

RELATED APPLICATIONS

This application is a national phase entry application of Patent Cooperation Treaty Application No. PCT/CA2019/051875, filed Dec. 20, 2019 (which designates the U.S.), which claims the benefit under 35 USC § 119 (e) from U.S. Provisional Application No. 62/783,341, filed on Dec. 21, 2018, both of which are incorporated herein by reference in their entirety.

FIELD OF THE DISCLOSURE

This disclosure relates to the culture of cells, and more specifically to the culture of immune-like cells or cells of the immune system. In particular, this disclosure relates to differentiation of immune-like cells or cells of the immune system.

BACKGROUND

Natural killer (NK) cells are lymphocytes that have an important role in immunity against infections and malignancies due to their ability to secrete proinflammatory cytokines and lyse virus-infected or tumor cells. NK cell-based cancer immunotherapy is a growing field. Allogeneic haploidentical NK cells are reactive against leukemia cells without causing graft-versus-host disease (GVHD). "Off-the-shelf" chimeric antigen receptor (CAR) engineered NK cells may offer a desirable alternative to autologous CAR T cells.

Due to the tumour killing property of NK cells, there is interest to develop methods for producing functional NK cells in quantities that are sufficient to address clinical needs, such as in immunotherapy applications. Expansion of peripheral blood (PB) or cord blood (CB) NK cells is a common method to produce sufficient number of NK cells required for these applications but these methods are difficult due to reliance on feeder cells and may result in NK cells exhaustion. In-vitro differentiation and expansion of NK cells from hematopoietic stem and progenitors (HSPCs) would provide a potentially much larger source of NK cells. In vitro generation of NK cells from HSPCs faces similar hurdles due to stromal-cell co-culture requirement and low expansions. Further, expanded NK cells should retain their cytotoxic properties.

Therefore, there is a need for robust methods to produce and expand NK cells from HSPCs in a stroma-free culture system while maintaining NK cells cytotoxic functions.

SUMMARY OF THE DISCLOSURE

The present disclosure relates to media and methods for differentiating NK progenitor cells, to obtain differentiated NK cells.

In one aspect of this disclosure, NK cell differentiation media are provided. In one embodiment, the NK cell differentiation medium comprises a pyrimidoindole compound. In one embodiment, the pyrimidoindole compound is either UM171 or UM729. In another embodiment, the concentration of the pyrimidoindole compound is between 10 nM and 3 μM. In one embodiment, the concentration of UM171 in the NK cell differentiation medium is about 100 nM. In one embodiment, the concentration of UM729 in the NK cell differentiation medium is about 1 μM.

In one embodiment the NK cell differentiation medium further comprises a basal medium. The basal medium may include salts, buffers, lipids, amino acids, trace elements, certain proteins, etc.

In one embodiment, the NK cell differentiation medium is supplemented with one or all of: one or more cytokines; one or more growth factors; or other proteins. The one or more cytokines may be SCF, FLT3L, IL-15, IL-2, IL-7, IL-3, IL-12 and IL-21. In one embodiment, the one or more cytokines may be either SCF or FLT3L, and IL-15. In one embodiment, the NK cell differentiation medium is supplemented with each of SCF, FLT3L, IL-15, IL-2, IL-7, IL-3, IL-12 and IL-21.

In one embodiment, the NK cell differentiation medium is not supplemented with an aryl hydrocarbon receptor antagonist. In another embodiment, the NK cell differentiation medium is not conditioned by contact with stromal cells or a stroma cell replacement.

In another embodiment, the NK cell differentiation medium is serum-free.

In yet another embodiment, the NK cell differentiation medium differentiates NK cell progenitors. The NK cell progenitors are preferably isolated or derived from a primary sample or derived from pluripotent stem cells, such as induced pluripotent stem cells.

In another aspect of this disclosure are provided methods for differentiating NK cells. An exemplary method may comprise, providing a population of NK cell progenitors in culture, and contacting the population of NK cell progenitors in culture with NK cell differentiation media as described above at a volume, concentration, and for a time sufficient to yield NK cells.

In one embodiment, contacting the population of NK cell progenitors with a pyrimidoindole compound is for about 1 week. In one embodiment, contacting with the pyrimidoindole compound is for at least 1 week. In one embodiment, contacting with the pyrimidoindole compound is for more than 1 week. In one embodiment, contacting with the pyrimidoindole compound is for about 2 weeks. In one embodiment, contacting with the pyrimidoindole compound is for more than 2 weeks.

In another embodiment, the population of NK cell progenitors is homogeneous for a phenotypic marker or is heterogeneous for a phenotypic marker. In one embodiment, the phenotypic marker is CD7. In another embodiment, the phenotypic marker is CD5.

In another embodiment, the NK cells increase in frequency during the contacting step.

In another embodiment, the NK cells increase in number during the contacting step.

In another embodiment, the population of NK cell progenitors increase or decrease in frequency or number during the contacting step.

In another embodiment, the providing and contacting steps are not in the presence of stromal cells or a stroma cell replacement.

In another embodiment, the providing and contacting steps are not in the presence of an aryl hydrocarbon receptor antagonist.

In another embodiment, the NK cells express CD56.

In another embodiment, the NK cells are cytotoxic.

In another embodiment, the population of NK cell progenitors is derived from a primary sample.

In another embodiment, the population of NK cell progenitors is isolated from a primary sample. In one embodiment, the primary sample is a cord blood sample, a bone marrow sample, or a peripheral blood sample.

In another embodiment, the population of NK cell progenitors is differentiated from a pluripotent stem cell(s).

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIG. 2(A) data points to STD). (B) The results of the 1 μM data points in FIG. 1(B) and FIG. 2(B) were normalized to STD cultures lacking the UM729 compounds. n=20, paired t-test on non-normalized data: p<0.0001 for frequency and p=0.006 for yield.

DETAILED DESCRIPTION

Figure 1:
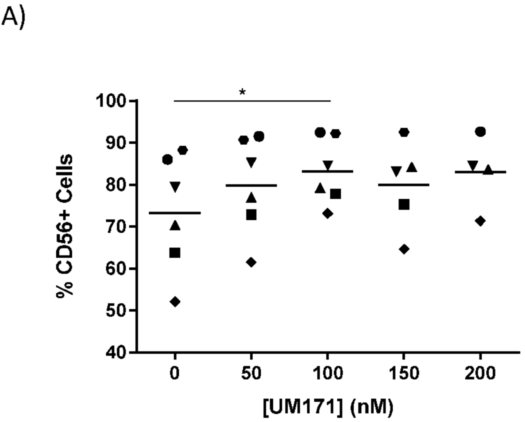
FIG. 1 shows the effects of pyrimidoindole compounds on the differentiation of $CD56^+$ NK cells from NK cell progenitors. (A) Frequency of $CD56^+$ NK cells after differentiating NK cell progenitors in culture for 14 days in the presence of a range of UM171 concentrations. At 100 nM, the frequency of NK cells is increased significantly compared to cultures lacking UM171 (paired t-test: p=0.013). (B) Frequency of $CD56^+$ NK cells after differentiating NK cell progenitors in culture for 14 days in the presence of a range of UM729 concentrations. At 1 μM, frequency of $CD56^+$ NK cells is increased significantly compared to cultures lacking UM729 (paired t-test: p=0.017). Results for cultures in the presence of 100 nM UM171 are also shown.
Figure 1:
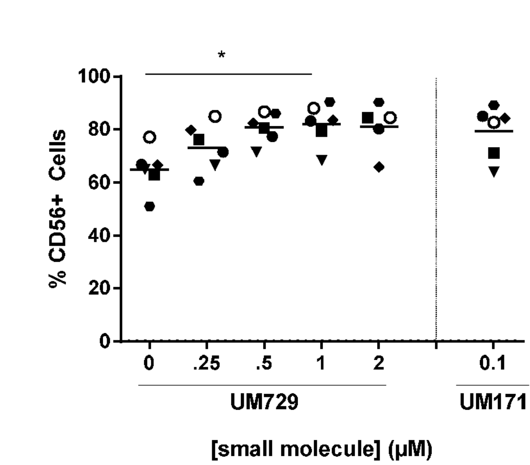

This disclosure relates to media and methods for differentiating NK progenitor cells, and to methods for obtaining differentiated NK cells.

Where used herein, "hematopoietic stem and progenitor cell" or "HSPC" means a cell of the hematopoietic lineage that is capable of self-renewal and/or differentiating into a more specialized cell of the hematopoietic lineage. HSPC may be obtained from bone marrow (BM), umbilical cord blood (CB), embryonic through to adult peripheral blood (PB), thymus, peripheral lymph nodes, gastrointestinal track, tonsils, gravid uterus, liver, or any other tissue having localized populations of HSPC. HSPC may also be differentiated from pluripotent stem cells such as induced pluripotent stem cells, embryonic stem cells, nave stem cells, extended stem cells, or the like. A hallmark of human HSPC is the expression of the transmembrane phosphoglycoprotein CD34, thus HSPC may be referred to as $CD34^+$ cells. Human HSPCs are defined by co-expression of CD45 and CD34 and may be further defined by combinations of markers such as CD38, CD43, CD45RO, CD45RA, CD10, CD49f, CD59, CD90, CD109, CD117, CD133, CD166, HLA-DR, CD201 and Integrin-alpha3, which may be used to distinguish HSPC subsets. HSPCs may lack expression, or have only low expression, of markers such as Glycophorin A, CD3, CD4, CD8, CD14, CD15, CD19, CD20 and CD56; such markers may be characteristic of mature blood cells.

Where used herein, "natural killer cell" or "NK cell" means a type of lymphocyte of the hematopoietic lineage that may derive from a HSPC. More specifically, NK cells may derive from multilymphoid progenitors (MLPs) or common lymphoid progenitors (CLPs). NK cells are typically characterized by: the absence of T and B cell-specific markers; the expression of CD56 and CD16 (low affinity Fc gamma receptor 3A, expressed on a subset of NK cells); and their effector functions. More specifically, effector functions of NK cells may include cytotoxicity and/or the production of IFNγ. NK cells may further be characterized by the expression of activating and inhibitory receptors referred to as killer immunoglobulin-like receptors (KIRs). Other activating receptors that NK cells may express include NKG2D and natural cytotoxicity receptors (NCRs) including NKp30, NKp44, and NKp46. The differentiation of HSPC to NK cells usually occurs via intermediate progenitors, such as an NK cell progenitor, but it may be possible to directly differentiate HSPC (or $CD34^+$ cells) to NK cells.

Where used herein, "natural killer cell progenitor" or "NK cell progenitor" means a cell type that is more specialized than a HSPC but is capable of further differentiating into a NK cell. An NK cell progenitor may be a direct descendant of a HSPC or may be further removed from a HSPC. Further, an NK cell progenitor may directly differentiate into a NK cell or may undergo one or more further steps of differentiation before becoming a NK cell. One example of a NK cell progenitor is a cell that is positive for the phenotypic markers CD7 and CD5. In another example, a NK cell progenitor may be positive for CD7 but negative for CD5. Other phenotypic markers that may be expressed by NK cell progenitors include CD10, CD45RA, CD34, CD38, CD161, CD122, CD117, and/or integrina4β7. CD34 may or may not be expressed on NK progenitors. Herein, unless explicitly stated, a population of NK cell progenitors may refer to a homogeneous population of cells or a heterogeneous population of cells capable of differentiating to a NK cell.

Where used herein, "pyrimidoindole compound" means a class of compounds which may be used to differentiate NK cells from a population of NK cell progenitors. In one embodiment the pyrimidoindole compound may be pyrimido[4,5-b]indole. In a specific embodiment, the pyrimidoindole compound may be UM171 as may be represented by the formula $C_{25}H_{27}N_9$ (X HBr [X $H_2O$], or otherwise referred to as (1r,4r)-$N^1$-(2-benzyl-7-(2-methyl-2H-tetrazol-5-yl)-9H-pyrimido[4,5-13]indol-4-yl)cyclohexane-1,4-diamine. In a different specific embodiment, the pyrimidoindole compound may be UM729 as may be represented by the formula $C_{20}H_{25}N_5O_2$·X HCl [X $H_2O$], or otherwise referred to as methyl 4-((3-(piperidin-1-yl)propyl)amino)-9H-pyrimido[4,5-b]indole-7-carboxylate. UM171 and UM729 are disclosed in U.S. Pat. No. 9,409,906 and UM729 is commercially available from STEMCELL Technologies.

Media

Media of this disclosure include any media which may be used to differentiate HSPC to NK cells, or may be used to differentiate a population of NK cell progenitors to NK cells. Such NK cell differentiation may refer to differentiation of HSPC to NK cells, which may include the derivation of one or more populations of NK cell progenitors therebetween. Or, NK cell differentiation may differentiate a population of NK cell progenitors directly or indirectly to NK cells.

Media of this disclosure may contain serum or may be serum-free. In one embodiment, media of this disclosure are serum-free. If the media are serum-free, it may be necessary to include in such media a serum replacement supplement, such as BIT 9500 Serum Substitute (STEMCELL Technologies, Catalogue #09500), or other commercially available serum replacement solutions. Alternatively, components ordinarily present in serum that are needed for culturing or differentiating any cells of this disclosure may be individually added at an acceptable concentration to the media.

Media of this disclosure will include a basal medium that is formulated as appropriate to culture the cells of this disclosure (e.g. HSPC, NK cell progenitors, NK cells). The basal medium may be any basal medium which is supportive of culturing cells of the hematopoietic lineage. By way of non-limiting example, the basal medium may be StemSpan™ SFEM (STEMCELL Technologies, Catalogue #09650), StemSpan™ SFEM II (STEMCELL Technologies, Catalogue #09655), StemSpan™-ACF (STEMCELL Technologies, Catalogue #09855), StemSpan™ H3000 (STEMCELL Technologies, Catalogue #09850), or any other commercially available basal medium fit for the purpose. Common components used to formulate such basal media may include salts, buffers, lipids, amino acids, trace elements, certain proteins, etc.

NK cell differentiation media of this disclosure may also include one or more pyrimidoindole compound. In one embodiment, the NK cell differentiation media includes only one pyrimidoindole compound. Examples of pyrimidoindole compounds include either UM171 or UM729. The concentration of the pyrimidoindole compound in the NK cell differentiation medium will depend on its nature. For example, some pyrimidoindole compounds may be more potent than others. For example, UM171 is reported as having approximately 10× the potency of UM729. Thus, to observe the same effects on differentiating NK cells from a population of NK cell progenitors, it may be necessary to include approximately a 10-fold higher concentration of UM729 versus UM171. In one embodiment, the concentration of the pyrimidoindole compound in the NK cell differentiation medium may be between 1 nM and 10 μM. In a more specific embodiment, the concentration of the pyrimidoindole compound in the NK cell differentiation medium may be between 5 nM and 5 μM. In a still more specific embodiment, the concentration of the pyrimidoindole compound in the NK cell differentiation medium may be between 10 nM and 3 μM. In a still more specific embodiment, the concentration of the pyrimidoindole compound in the NK cell differentiation medium may be between 30 nM and 2 μM. In a still more specific embodiment, the concentration of the pyrimidoindole compound in the NK cell differentiation medium may be between 50 nM and 1 μM. In a still more specific embodiment, the concentration of the pyrimidoindole compound in the NK cell differentiation medium may be between 75 nM and 500 nM. In a still more specific embodiment, the concentration of the pyrimidoindole compound in the NK cell differentiation medium may be between 90 nM and 150 nM.

In embodiments where the pyrimidoindole compound is UM171, its concentration in the NK cell differentiation medium may be between about 10 nM and 1000 nM, or between about 20 nM and 500 nM, or between about 50 nM and 200 nM. In a specific embodiment, the concentration of UM171 in the NK cell differentiation medium is about 100 nM.

In embodiments where the pyrimidoindole compound is UM729, its concentration in the NK cell differentiation medium may be between about 50 nM and 10 μM, or between about 100 nM and 5 μM, or between about 250 nM and 2.50 μM. In a specific embodiment, the concentration of UM729 in the NK cell differentiation medium is about 1 μM.

An NK cell differentiation medium of this disclosure may need to be further supplemented in order to culture the cells of this disclosure (e.g. HSPC, NK cell progenitors, NK cells). The supplement(s) added to the basal media may vary depending on the specific type of cell to be cultured. In general, a non-exhaustive list of potential supplements includes one or more cytokines, one or more growth factors, or other proteins.

Specifically, SCF, FLT3L, IL-3, IL-2, IL-7, IL-15, IL-12 and IL-21 may be included in NK cell differentiation media. In one embodiment the NK cell differentiation medium is supplemented with each of FLT3L, SCF, IL-3, IL-15, IL-2, IL7, IL-12 and IL-21. In one embodiment, the NK cell differentiation medium is supplemented with one or more of FLT3L, SCF, IL-3, IL-2, IL-15, IL-7, IL-12 and IL-21. In one embodiment, the NK cell differentiation medium is supplemented with one or more of FLT3L, SCF, IL-15 and IL-7. In one embodiment, the NK cell differentiation medium is supplemented with either FLT3L or SCF, and IL-15. In embodiments of NK cell differentiation media that include one or more of SCF, FLT3L, IL-3, IL-7, IL-2, IL-15, IL-12 and IL-21, such cytokines may be present at concentrations between about 1-1000 ng/mL, or about 1-100 ng/mL, or about 5-50 ng/mL, and IL-2 may be present at about 50-1500 IU/mL.

In some embodiments, any one or more of SCF, FLT3L, IL-3, IL-2, IL-7, IL-15, IL-12 and IL-21 may not be included, however, the efficiency of the NK cell differentiation medium may be compromised. In one embodiment, the inclusion of IL-15 in the NK cell differentiation medium is required for differentiating NK cells from a population of NK cell progenitors using an NK cell differentiation medium.

Further, a NK cell differentiation medium of this disclosure may synergize with additional supplements. For example, on the one hand, stromal cells may be used together with cell culture media of this disclosure. Non-exhaustive examples of stromal cells include the embryonic liver cell line EL08.1D2, AFT024 cells, OP9 cells, or M2-10B4 cells. On the other hand, stroma-free culture approaches may be used together with cell culture media of this disclosure. Stroma-free culture systems may utilize medium previously conditioned by stromal cells, or such a system may utilize a stroma cell replacement. A stroma cell replacement may comprise one or more defined components which provide appropriate signals or attachment sites to cells in culture. Such components may be included in a coating applied to an inner culture surface of a culture vessel or on solid surfaces suspended in a cell culture media, such as on particles, beads, microcarriers, or the like. Non-exhaustive examples of such components may include fibronectin coatings, whether full-length or a fragment thereof, VCAM-1, an immobilized Notch ligand, or coatings such as StemSpan™ Lymphoid Differentiation Coating Supplement (STEMCELL Technologies, Catalogue #09925). Or, stroma cell replacement may provide such components in soluble form within a cell culture media, such as by supplementation or as a medium previously conditioned by stromal cells.

While the inclusion of stromal cells or a stroma cell replacement may be required for the differentiation of HSPC to NK cell progenitors, stromal cells or stroma cell replacement may be dispensable for the differentiation of NK cell progenitors to NK cells. In a preferred embodiment, an NK cell differentiation medium (i.e. a medium for differentiating NK cell progenitors to NK cells) is not conditioned by contact with stromal cells or a stroma cell replacement. Thus, such an NK cell differentiation medium would not have been or be in contact with stromal cells or a stroma cell replacement.

Compounds other than pyrimidoindole compounds are reported to play a role in cultures of various types of hematopoietic cells. For example, compounds in the class of aryl hydrocarbon receptor antagonists may be included in the NK cell differentiation medium. Some examples of aryl hydrocarbon receptor antagonists include StemRegenin 1 (SR1) (STEMCELL Technologies, Catalogue #72342) or CH223191 (STEMCELL Technologies, Catalogue #72732). In embodiments where CH223191 is included in an NK cell differentiation medium, the compound may be present at concentrations ranging between about 100 nM and 10 μM, or between about 500 nM and 8 μM, or between about 1 μM and 6 μM. In a specific embodiment, the concentration of CH223191 is about 5 μM.

In one embodiment, the NK cell differentiation medium does not include an aryl hydrocarbon receptor antagonist.

Therefore, in one aspect of this disclosure is provided a NK cell differentiation medium. The NK cell differentiation medium may be used to differentiate NK cells from HSPC or a population of NK cell progenitors. The NK cell differentiation medium may comprise a basal medium (as described above) and a pyrimidoindole compound (as described above). In one embodiment, the basal medium is StemSpan™ SFEM II (STEMCELL Technologies, Catalogue #09655) and the pyrimidoindole compound is either UM171 or UM729. Such an NK cell differentiation medium is serum-free while further comprising one or more of SCF, FLT3L, IL-15, IL-2, IL-3 IL-7, IL-12 and IL-21

Where it is important to obtain a significant quantity of differentiated NK cells it may be desirable to first culture and expand HSPC, prior to differentiating the HSPC to NK cell progenitors and NK cells.

HSPC may be expanded by any known method known in the art. In one embodiment, the HSPC may be expanded to significant numbers using StemSpan™ SFEM II (STEMCELL Technologies, Catalogue #09655) supplemented with the StemSpan™ CD34$^+$ Expansion Supplement (STEMCELL Technologies, Catalogue #02691) or StemSpan™ CC100 (STEMCELL Technologies, Catalog #02690) or StemSpan™ CC110 (STEMCELL Technologies, Catalog #02697) according to the manufacturer's protocol. Expansion of HSPC using StemSpan™ SFEM II (STEMCELL Technologies, Catalogue #09655) and supplemented with an expansion supplement, or any other appropriate medium, may be further enhanced by supplementing the medium with a pyrimidoindole compound such as UM171 or UM729.

The concentration of the pyrimidoindole compound in the HSPC expansion protocol will depend on its nature. For example, some pyrimidoindole compounds may be more potent than others. For example, UM171 is reported as having approximately 10× the potency of UM729. Thus, to observe the same effects using different pyrimidoindole compounds, it may be necessary to include a 10-fold higher concentration of UM729 versus UM171. In one embodiment, the concentration of the pyrimidoindole compound in the HSPC expansion protocol may be between 1 nM and 10 μM. In a more specific embodiment, the concentration of the pyrimidoindole compound in the HSPC expansion protocol may be between 5 nM and 5 μM. In a still more specific embodiment, the concentration of the pyrimidoindole compound in the HSPC expansion protocol may be between 10 nM and 3 μM. In a still more specific embodiment, the concentration of the pyrimidoindole compound in the HSPC expansion protocol may be between 30 nM and 2 μM. In a still more specific embodiment, the concentration of the pyrimidoindole compound in the HSPC expansion protocol may be between 50 nM and 1 μM. In a still more specific embodiment, the concentration of the pyrimidoindole compound in the HSPC expansion protocol may be between 75 nM and 500 nM. In a still more specific embodiment, the concentration of the pyrimidoindole compound in the HSPC expansion protocol may be between 90 nM and 150 nM.

A medium for expanding HSPC may further comprise an aryl hydrocarbon receptor antagonist. Some examples of aryl hydrocarbon receptor antagonists include StemRegenin 1 (SR1) (STEMCELL Technologies, Catalogue #72342) or CH223191 (STEMCELL Technologies, Catalogue #72732). In embodiments where CH223191 is included in an HSPC expansion medium, the compound may be present at concentrations ranging between about 100 nM and 10 μM, or between about 500 nM and 8 μM, or between about 1 μM and 6 μM. In a specific embodiment, the concentration of CH223191 is about 5 μM.

HSPC, whether or not expanded as described above, may be cultured in a first medium to generate a transitory population of NK cell progenitors. The first medium (i.e. NK cell progenitor differentiation medium) may be essentially as described above for the NK cell differentiation medium, and the addition of a pyrimidoindole compound is optional. In such an embodiment the pyrimidoindole compound may be UM171 or UM729. In one embodiment, the NK cell progenitor medium is devoid of an added pyrimidoindole compound.

An NK cell progenitor differentiation medium of this disclosure may synergize with additional supplements. For example, on the one hand, stromal cells may be used along with such a cell culture media. Non-exhaustive examples of stromal cells include the embryonic liver cell line EL08.1D2, AFT024 cells, OP9 cells, or M2-10B4 cells. On the other hand, stroma-free culture approaches may be used along with such a cell culture media. Stroma-free culture systems may utilize medium previously conditioned by stromal cells, or such a system may utilize a stroma cell replacement. A stroma cell replacement may comprise one or more defined components which provide appropriate signals or attachment sites to cells in culture. Such components may be included in a coating applied to an inner culture surface of culture vessel or on solid surfaces suspended in a cell culture media, such as on particles, beads, microcarriers, or the like. Non-exhaustive examples of such components may include fibronectin coatings, whether full-length or a fragment thereof, VCAM-1, an immobilized Notch ligand, or coatings such as StemSpan™ Lymphoid Differentiation Coating Supplement (STEMCELL Technologies, Catalogue #09925). Or, stroma cell replacement may provide such components in soluble form within a cell culture media, such as by supplementation or as a medium previously conditioned by stromal cells.

In one embodiment, the NK cell progenitor differentiation medium is in contact with stromal cells (or has been conditioned by a culture of stromal cells) or comprises stroma cell replacement. For example, the stroma cell replacement may be a fibronectin coating, whether full-length or a fragment thereof, VCAM-1, an immobilized Notch ligand, or a coating such as StemSpan™ Lymphoid Differentiation Coating Supplement (STEMCELL Technologies, Catalogue #09925).

Therefore, in another aspect of this disclosure is provided a NK cell progenitor differentiation medium, in accordance with the foregoing. Such a medium may be used to differentiate HSPC to a population of NK cell progenitors. Thusly derived NK cell progenitors may continue to be cultured in the NK cell progenitor differentiation medium to obtain differentiated NK cells, or they may be sequentially cultured in the NK cell differentiation medium described above.

Methods

The methods of this disclosure encompass those steps for differentiating NK cells from a population of NK cell progenitors. The methods of this disclosure may also encompass those steps for differentiating HSPC to NK cells, whether or not via one or more NK cell progenitor intermediate populations. The methods disclosed herein for differentiating NK cells are preferably in vitro methods.

The methods of this disclosure may begin by providing an appropriate starting population of cells. If beginning from HSPC, the HSPC may be commercially purchased, isolated from a blood or tissue sample, or derived (i.e. differentiated) from a pluripotent stem cell, such as an induced pluripotent stem cell. Regardless of the source of the HSPC, it may be necessary to perform one or more purification experiments to eliminate as many contaminating cells as possible. Samples comprising HSPC may be cleared of contaminating cells by any known approach. For example, such samples may be subjected to density gradient centrifugation or to positive and/or negative cell selection. An exemplary approach may include a conventional negative selection of mononuclear cells using a RosetteSep™ reagent, for example RosetteSep™ Cord Blood CD34 Pre-Enrichment Cocktail STEMCELL Technologies, Catalogue #15896C), followed by positive selection of CD34$^+$ HSPC using an appropriate EasySep™ reagent, for example EasySep™ Human CD34 Positive Selection Kit II (STEMCELL Technologies, Catalogue #17896).

Depending on the number of NK cells needed, it may be desirable to first expand the HSPC prior to the differentiation thereof into NK cells (whether or not via one or more populations of NK cell progenitors). HSPC may be expanded using any known approach. An exemplary approach to expanding HSPC may include culturing the HSPC in the presence of an appropriate basal medium and the StemSpan™ CD34$^+$ Expansion Supplement (STEMCELL Technologies, Catalogue #02691) or StemSpan™ CC100 (STEMCELL Technologies, Catalogue #02690) or StemSpan™ CC110 (STEMCELL Technologies, Catalogue #02697). Using the foregoing approach, an appropriate basal medium may include StemSpan™ SFEM (STEMCELL Technologies, Catalogue #09650), StemSpan™ SFEM II (STEMCELL Technologies, Catalogue #09655), StemSpan™-ACF (STEMCELL Technologies, Catalogue #09855), StemSpan™ H3000 (STEMCELL Technologies, Catalogue #09850) serum-free expansion media.

Whether or not the HSPC are subjected to a prior expansion, the HSPC may be differentiated to a population of NK cell progenitors. The population of NK cell progenitors may be a homogeneous population of cells or a heterogeneous population of cells. For example, a homogeneous population of NK cell progenitors may be characterized by a CD7$^+$CD5$^+$ or a CD7$^+$CD5$^-$ phenotype. And, a heterogeneous population of NK cell progenitors may include those cells having CD7$^+$CD5$^+$, CD7$^+$CD5$^-$, CD7$^-$CD5$^-$ phenotypes. In one embodiment, the NK cell progenitors (e.g. CD7$^+$CD5$^+$, CD7$^+$CD5$^-$, and/or CD7$^-$CD5$^-$ cells) may be either CD34$^+$ or CD34$^-$.

In some embodiments, it may not be necessary to derive NK cell progenitors from HSPC. In one embodiment, it may desirable to directly differentiate HSPC to NK cells using a medium of this disclosure. In one embodiment, it may be desirable to directly differentiate pluripotent stem cells, including but not limited to induced pluripotent stem cells, to NK cells using a medium of this disclosure. In one embodiment, it may be desirable to transdifferentiate cells corresponding to a particular germ layer to NK cells using a medium of this disclosure. In some of these embodiments it may be necessary to further supplement the media with additional factors or cytokines and/or transcription factors, whether in the form of protein or nucleic acid, or activators of such transcription factors.

If differentiating HSPC to a population of NK cell progenitors, this may be carried out by contacting the population of HSPC with an appropriate culture medium. The appropriate culture medium may be any known medium capable of differentiating HSPC to a population of NK cell progenitors. In one embodiment, HSPC are differentiated to a population of NK cell progenitors by contacting the HSPC with a NK cell progenitor differentiation medium as described above. In a different embodiment, the NK cell progenitor differentiation medium may comprise StemSpan™ SFEM II (STEMCELL Technologies, Catalogue #09655) supplemented with Lymphoid Progenitor Expansion Supplement (STEMCELL Technologies, Catalogue #09915). In one embodiment, the HSPC contacted with the NK cell progenitor differentiation medium may be cultured using the StemSpan™ Lymphoid Differentiation Coating Supplement (STEMCELL Technologies, Catalogue #09925), or any other known coating useful for differentiating HSPC to a population of NK cell progenitors.

In another aspect, the methods of this disclosure may commence by providing a population of NK cell progenitors, such as may be differentiated or derived from HSPC or induced pluripotent stem cells using, for example, a NK cell progenitor differentiation medium as described above, or as may be directly isolated from primary samples (e.g. cord blood, peripheral blood, bone marrow, thymus, uterus, liver, gut or secondary lymphoid tissues) on the basis of a distinguishing phenotypic marker (e.g. CD7 and/or CD5±CD34). In one embodiment, the population of NK cell progenitors may be derived (i.e. differentiated), in which case such population of NK cell progenitors is derived from a primary sample or a pluripotent stem cell, such as an induced pluripotent stem cell or an ES cell. In one embodiment, the population of NK cell progenitors may be isolated from a primary sample. Cell isolation approaches are known in the art, and may include either positive or negative cell selection, or both. By way of non-limiting example, lineage positive cells may be depleted (such as with RosetteSep™ Human Hematopoietic Progenitor Cell Enrichment Cocktail, STEMCELL Technologies, Catalog #15066) and NK cell progenitors may be isolated by selecting cells expressing one or more of the following markers: CD34, CD38, CD45RA, CD10, CD7, and CD5. Thus, in one embodiment the population of NK cell progenitors expresses CD7. In another embodiment, the population of NK cell progenitors may express both CD7 and CD5. In another embodiment, the population of NK cell progenitors may only express CD7 and not express CD5. In another embodiment, the population of NK cell progenitors may or may not express CD34.

In another embodiment, the population of NK cell progenitors may be differentiated from a pluripotent stem cell (PSC). The differentiation of PSC-derived NK cell progenitors may require the differentiation of one or more intermediate populations of cells, such as PSC-derived CD34$^+$ HSPC.

Differentiating the population of NK cell progenitors to NK cells may be carried out by contacting the population of NK cell progenitors in culture with a pyrimidoindole compound at a concentration and for a time sufficient to yield NK cells. The pyrimidoindole compound may be included in any medium that supports the population of NK cell progenitors. In one embodiment, the pyrimidoindole compound is included in a NK cell differentiation medium in accordance with this disclosure.

As described above, the concentration of the pyrimidoindole compound in the NK cell differentiation medium will depend on its nature. For example, some pyrimidoindole compounds may be more potent than others. For example, UM171 is reported as having approximately 10× the potency of UM729. Thus, to observe the same effects on differentiating NK cells from a population of NK cell progenitors, it may be necessary to include a 10-fold higher concentration of UM729 versus UM171. In one embodiment, the concentration of the pyrimidoindole compound in the NK cell differentiation medium may be between 1 nM and 10 μM. In a more specific embodiment, the concentration of the pyrimidoindole compound in the NK cell differentiation medium may be between 5 nM and 5 μM. In a still more specific embodiment, the concentration of the pyrimidoindole compound in the NK cell differentiation medium may be between 10 nM and 3 μM. In a still more specific embodiment, the concentration of the pyrimidoindole compound in the NK cell differentiation medium may be between 30 nM and 2 μM. In a still more specific embodiment, the concentration of the pyrimidoindole compound in the NK cell differentiation medium may be between 50 nM and 1 μM. In a still more specific embodiment, the concentration of the pyrimidoindole compound in the NK cell differentiation medium may be between 75 nM and 500 nM. In a still more specific embodiment, the concentration of the pyrimidoindole compound in the NK cell differentiation medium may be between 90 nM and 150 nM.

Also as described above, in embodiments where the pyrimidoindole compound is UM171, its concentration in the NK cell differentiation medium may be between about 10 nM and 1000 nM, or between about 20 nM and 500 nM, or between about 50 nM and 200 nM. In a specific embodiment, the concentration of UM171 in the NK cell differentiation medium is about 100 nM.

Also as described above, in embodiments where the pyrimidoindole compound is UM729, its concentration in the NK cell differentiation medium may be between about 50 nM and 10 μM, or between about 100 nM and 5 μM, or between about 250 nM and 2.50 μM. In a specific embodiment, the concentration of UM729 in the NK cell differentiation medium is about 1 μM.

Other potential embodiments of NK cell differentiation media are as described above.

A pyrimidoindole compound-comprising NK cell differentiation medium may increase the frequency and/or yield of NK cells differentiated from a population of NK cell progenitors. During NK cell differentiation, the frequency and/or yield of NK cell progenitors may decrease as the frequency and yield of NK cells increases. Thus, the inclusion of a pyrimidoindole compound in a NK cell differentiation medium may be important for improving the efficiency of differentiating NK cells from a population of NK cell progenitors in culture. The effects of a pyrimidoindole compound may be specific to NK cell progenitors, as including pyrimidoindole compounds in a medium for differentiating NK cell progenitors (such as an NK cell progenitor differentiation medium) from, for example, HSPC, may have an overall inhibitory effect on the yield and frequency of thusly derived NK cell progenitors. However, including a pyrimidoindole compound in a medium for differentiating NK cells from a population of NK cell progenitors in culture (such as an NK cell differentiation medium) may rescue or compensate the inhibitory effect of a pyrimidoindole compound that may have been included in a medium for differentiating NK cell progenitors (such as an NK cell progenitor differentiation medium) from a population of HSPC, whether primary or differentiated from pluripotent stem cells, such as induced pluripotent stem cells or ES cells.

If differentiating NK cells by providing a population of NK cell progenitors and contacting such population of NK cell progenitors in culture with a pyrimidoindole compound to yield NK cells, the providing and contacting steps may be carried out in the presence or in the absence of stromal cells or a stroma cell replacement. In one embodiment, the population of NK cell progenitors are differentiated to NK cells in the absence of stromal cells or a stroma cell replacement.

Furthermore, if differentiating NK cells by providing a population of NK cell progenitors and contacting such population of NK cell progenitors in culture with a pyrimidoindole compound to yield NK cells, the providing and contacting steps may be carried out in the presence or in the absence of an aryl hydrocarbon receptor agonist, such as StemRegenin 1 (SR1) (STEMCELL Technologies, Catalogue #72342) or CH223191 (STEMCELL Technologies, Catalogue #72732). In one embodiment, the population of NK cell progenitors are differentiated to NK cells in the absence of an aryl hydrocarbon receptor antagonist.

Contacting the population of NK cell progenitors in culture with a pyrimidoindole compound may be for any amount of time that is sufficient to yield NK cells from the population of NK cell progenitors. Recognizing that the pyrimidoindole compound in the basal medium (or other components of the basal medium or supplemented basal medium) may be depleted over time, it may be necessary to perform media changes at regular intervals, such as daily, every other day, every two days, every three days, every four days, every five days, every six days, every seven days, or less frequently, or at different frequencies such as every 1-2 days, every 2-3 days, or every 3-4 days, and so forth. The number of media changes performed may directly correlate to the duration of the method for differentiating NK cells. In one embodiment, the duration of the method for differentiating NK cells from NK cell progenitors (i.e. the duration of time a population of NK cell progenitors is contacted with a pyrimidoindole compound) is about 1 week. In another embodiment, the duration of the method for differentiating NK cells from NK cell progenitors is at least 1 week. In another embodiment, the duration of the method for differentiating NK cells from NK cell progenitors is more than 1 week. In another embodiment, the duration of the method for differentiating NK cells from NK cell progenitors is about 2 weeks. In another embodiment, the duration of the method for differentiating NK cells from NK cell progenitors is more than 2 weeks.

Through contacting the population of NK cell progenitors in culture with a pyrimidoindole compound, the NK cells may increase in frequency. An increase in frequency of NK cells means an increase in the proportion of NK cells relative to the proportion of all cells in the culture at one time point compared to an earlier time point. For example, if the expression of CD56 is used as a proxy for differentiated NK cells, the frequency of NK cells at any given time is determined according to the formula: # of $CD56^+$ cells/(# of $CD56^+$ cells+# of $CD56^-$ cells).

Also, through contacting the population of NK cell progenitors in culture with a pyrimidoindole compound, the NK cells may increase in number (i.e. yield). An increase in the number of NK cells means an increase in the number of NK cells at one point time point compared to an earlier time point. For example, if the expression of CD56 is used as a proxy for differentiated NK cells, the number of NK cells at any given time is determined by counting the # of CD56$^{+}$ cells.

The NK cells differentiated in accordance with the methods disclosed herein may express the phenotypic marker CD56. For example, about 40% of the differentiated NK cells of this disclosure may be CD56$^{+}$. Or, about 50% of the differentiated NK cells of this disclosure may be CD56$^{+}$. Or, about 60% of the differentiated NK cells of this disclosure may be CD56$^{+}$. Or, about 70% of the differentiated NK cells of this disclosure may be CD56$^{+}$. Or, more than 70% of the differentiated NK cells of this disclosure may be CD56$^{+}$. Or, more than 80% of the differentiated NK cells of this disclosure may be CD56$^{+}$. In a specific embodiment, >70% of the differentiated NK cells of this disclosure are CD56$^{+}$.

The NK cells differentiated in accordance with the methods disclosed herein may also express natural cytotoxicity markers, such as NKp30 and/or NKp44 and/or NKp46. Accordingly, the differentiated NK cells of the disclosure may be cytotoxic. In a standard cytotoxicity assay, the differentiated NK cells of the disclosure may exhibit cytotoxicity toward a target cell. In a specific embodiment, the target cell may be the K562 cell line, and the differentiated NK cells of this disclosure may achieve a killing ability comparable to NK cells isolated from peripheral blood of adult donors. For example, NK cells isolated from peripheral blood of adult donors may achieve a % specific lysis of about 90%, or about 80%, or about 70%, or about 60%, or about 50%, or about 40%, or about 30%. In a specific embodiment, the differentiated NK cells of this disclosure and NK cells isolated from peripheral blood of adult donors each achieve a killing ability of about 70%. In some embodiments, it may be desirable to first activate the differentiated NK cells prior to carrying out a killing assay. The skilled artisan will appreciate how to activate NK cells, which may include exposing NK cells to IL-2 or IL-15 for a sufficient amount of time.

The NK cells differentiated in accordance with methods disclosed herein may also express other markers associated with mature NK cells, such as NKG2D and/or CD16 and/or CD94 and/or KIRs.

The NK cells differentiated in accordance with methods disclosed herein may also produce IFNγ upon appropriate stimulation, such as with PMA/Ionomycin. Intracellular IFNγ may be detected following treatment with Brefeldin A. In one embodiment, about 30% of the differentiated NK cells of this disclosure having been appropriately stimulated produce intracellular IFNγ. In another embodiment, about 40% of the differentiated NK cells of this disclosure having been appropriately stimulated produce intracellular IFNγ. In another embodiment, about 50% of the differentiated NK cells of this disclosure having been appropriately stimulated produce intracellular IFNγ. In another embodiment, about 60% of the differentiated NK cells of this disclosure having been appropriately stimulated produce intracellular IFNγ. In another embodiment, about 70% of the differentiated NK cells of this disclosure having been appropriately stimulated produce intracellular IFNγ. In another embodiment, about 80% of the differentiated NK cells of this disclosure having been appropriately stimulated produce intracellular IFNγ. In another embodiment, about 90% of the differentiated NK cells of this disclosure having been appropriately stimulated produce intracellular IFNγ. In another embodiment, more than 90% of the differentiated NK cells of this disclosure having been appropriately stimulated produce intracellular IFNγ.

Importantly, a majority of the NK cells differentiated in accordance with methods disclosed herein do not express certain markers associated with the T cell lineage. In one embodiment, less than 5% of the differentiated NK cells of this disclosure express CD3. In another embodiment, less than 4% of the differentiated NK cells of this disclosure express CD3. In another embodiment, less than 3% of the differentiated NK cells of this disclosure express CD3. In another embodiment, less than 2% of the differentiated NK cells of this disclosure express CD3. In another embodiment, less than 1% of the differentiated NK cells of this disclosure express CD3. The absence, or essentially the absence of CD3 expression among the differentiated NK cells of this disclosure suggests they are not T cells or NKT cells.

By practicing the above described methods it may be possible to obtain large quantities of in vitro differentiated NK cells. Such in vitro differentiated NK cells may be used in downstream cell therapy applications. Prior to using such in vitro differentiated NK cells, it may be desirable to make such NK cells transgenic, such as by gene editing technology. If wishing to generate transgenic NK cells, it may thus be desirable to clonally expand a transgenic HSPC or a transgenic NK cell progenitor prior to differentiating the population of NK cell progenitors to NK cells using media and methods of this disclosure.

The following non-limiting examples are illustrative of the present disclosure.

EXAMPLES

Example 1: Preparation and Culture of Cells

Human CB samples were obtained from Bloodworks NW (Seattle, WA) and CD34$^{+}$ cells were isolated using EasySep™ Human Cord Blood CD34 Positive Selection Kit II (STEMCELL Technologies, Catalogue #17896). Obtained in this way the purity of CD34$^{+}$ cells is typically higher than 90%.

The wells of a 24-well plate were coated with StemSpan™ Lymphoid Differentiation Coating Supplement (STEMCELL Technologies, Catalogue #09925) and 5000 CD34$^{+}$ cells were plated per well. The CD34$^{+}$ cells were cultured for up to 14 days in StemSpan™ SFEM II (STEMCELL Technologies, Catalogue #09605, 09655) supplemented with Lymphoid Progenitor Expansion Supplement (STEMCELL Technologies, Catalogue #09915) with media changes every 3-4 days.

After 14 days in culture, CD34$^{+}$ cell-derived NK cell progenitors were harvested. 50,000 NK cell progenitors were plated per well of an uncoated tissue culture 24-well plate. The plated NK cell progenitors were cultured for up to two weeks in NK Cell Differentiation medium (i.e StemSpan™ SFEM II (STEMCELL Technologies, Catalog # 09605, 09655) supplemented with NK Cell Differentiation Supplement (STEMCELL Technologies, Catalogue #09950), and cultured for an additional two weeks with media changes every 3-4 days. UM729 or UM171 was added to supplemented NK Cell Differentiation Medium on days 14-28. On day 28 cells were harvested for analysis or downstream applications.

Figure 2:
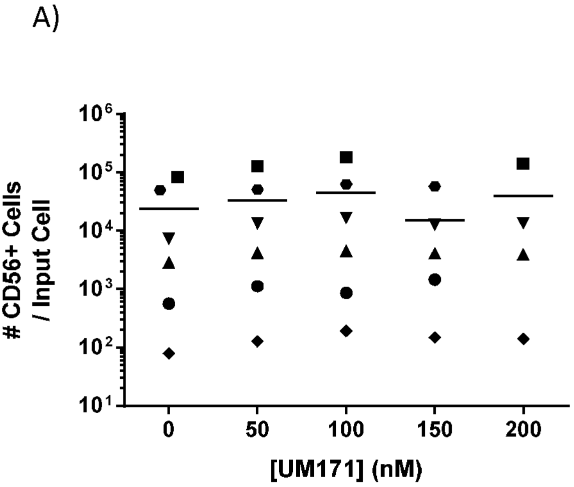
FIG. 2 shows the effects of pyrimidoindole compounds on the differentiation of $CD56^+$ NK cells from NK cell progenitors. (A) Yield of $CD56^+$ NK cells per input cell (i.e. day 0 cells) after differentiating NK cell progenitors in culture for 14 days in the presence of a range of UM171 concentrations. (B) Yield of $CD56^+$ NK cells per input cell (i.e. day 0 cells) after differentiating NK cell progenitors in culture for 14 days in the presence of a range of UM729 concentrations. At 1 μM, yield of $CD56^+$ NK cells is increased significantly compared to cultures lacking UM729 (paired t-test: p=0.032). Results for cultures in the presence of 100 nM UM171 are also shown.
Figure 2:
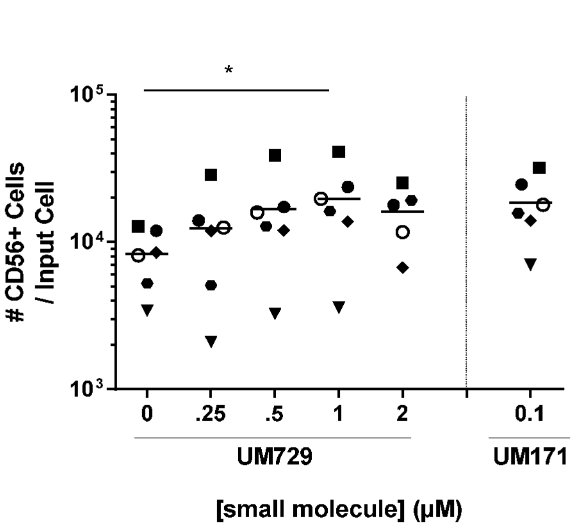

Harvested cells were stained and measured by flow cytometry for expression of the NK cell lineage marker CD56. Dead cells were excluded by light scatter profile and 7-AAD or DRAQ7 staining. The results in FIGS. 1 and 2 at condition "0" (plotted on the x-axis) indicate the frequency and yield of CD56$^{+}$ NK cells that result from experiments that follows the protocol described above but in the absence of UM171 or UM729. Cell counts were obtained using the NucleoCounter NC250. Yield was calculated by dividing the resulting cell number by the number of cells initially seeded. Yields of specific cell types were obtained by multiplying total yield by cell frequency.

Example 2: Effect of Pyrimidoindole Compounds on NK Cell Differentiation

Cells were cultured as described in Example 1, with the exception that the up to two week culture of NK cell progenitors (i.e. culture days 14-28) in NK Cell Differentiation medium occurred in the presence or absence of UM171 or UM729.

The effects of UM171 and UM729 were tested across a range of concentrations: 0 nM, 50 nM, 100 nM, 150 nM and 200 nM for UM171; and 0 μM, 0.25 μM, 0.5 μM, 1 μM, and 2 μM for UM729. The results of these experiments are summarized in FIGS. 1 and 2.

The frequency of $CD56^+$ NK cells appeared to be highest at a concentration of 100 nM for UM171 (FIG. 1A) and at a concentration of 1 μM for UM729 (FIG. 1B). The yield of $CD56^+$ NK cells also appeared to be highest at a concentration of 100 nM for UM171 (FIG. 2A) and at a concentration of 1 μM for UM729 (FIG. 2A). Based on these results a concentration of 100 nm for UM171 and 1 μM for UM729 was selected for further experiments.

Figure 3:
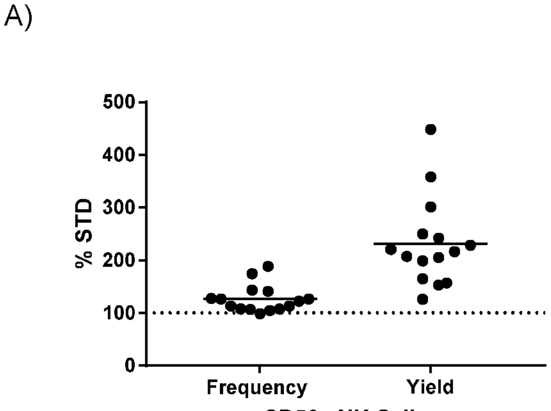
FIG. 3 shows the effects of the presence or absence of pyrimidoindole compounds on the differentiation of $CD56^+$ NK cells from NK cell progenitors. (A) The results of the 100 nM data points in FIG. 1(A) and FIG. 2(A) were normalized to standard ("STD") cultures lacking the UM171 compound. n=15, paired t-test on non-normalized data: p=0.0001 for frequency and p=0.052 for yield (i.e.
Figure 3:
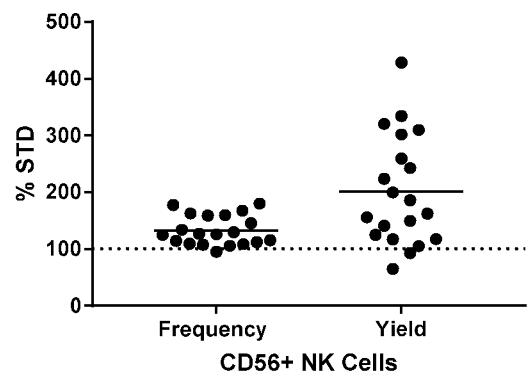

Thus, the addition of UM171 or UM729 to differentiation cultures of NK cell progenitors increased the frequency of $CD56^+$ NK cells at increasing concentrations of these molecules: up to 100 nM for UM171 and 1 μM for UM729. Overall, the average frequency and yield of NK cells increased by on average ~30% and 2 fold in culture conditions including 100 nM UM171 (FIG. 3A) or 1 μM UM729 (FIG. 3B) compared to culture conditions not including a pyrimidoindole compound.

Example 3: Expression of Natural Cytotoxicity Receptors on Differentiated NK Cells $CD56^+$ NK cells were differentiated as described in Examples 1 and 2 in the presence of 1 μM UM729 and analyzed on day 28 by flow cytometry for the expression of known NK cell markers. Cells were stained with fluorescence-conjugated antibodies against indicated NK cell markers for 15 min at 4° C. Non-specific binding was blocked using FcR blocker and 5% human or rat serum. Dead cells were excluded by light scatter profile and 7-AAD or DRAQ7 staining. Prepared samples were analyzed by flow cytometry.

Figure 4:
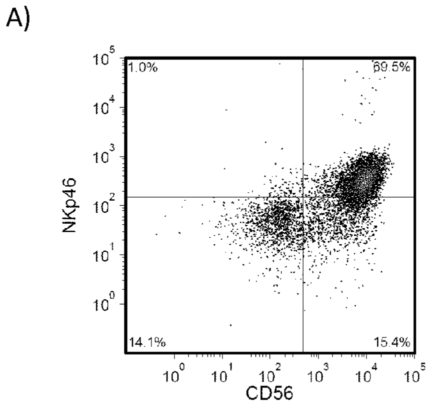
FIG. 4 shows the expression of natural cytotoxicity receptors on the surface of differentiated $CD56^+$ NK cells. Cells were analyzed by flow cytometry for the expression of (A) NKp46, (B) NKp44, and (C) NKp30.
Figure 4:
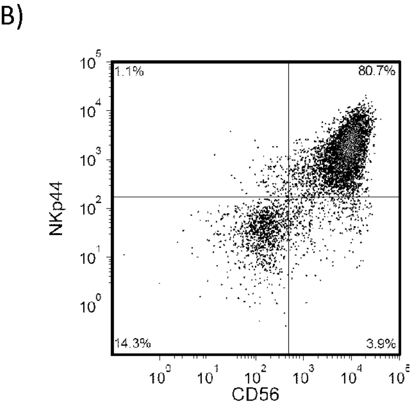
Figure 4:
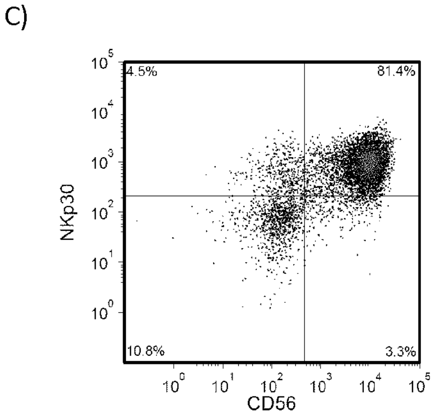

The results show that: approximately 70% of analyzed cells co-express CD56 and NKp46 (FIG. 4A); approximately 80% of analyzed cells co-express CD56 and NKp44 (FIG. 4B); and approximately 80% of analyzed cells co-express CD56 and NKp30 (FIG. 4C).

Example 4: Expression of Markers Associated with More Mature NK Cells on Differentiated NK Cells $CD56^+$ NK cells were differentiated as described in Examples 1 and 2 in the presence of 1 μM UM729 and analyzed on day 28 by flow cytometry for the expression of known NK cell markers. The cells were stained for the markers described in this Example essentially as described in Example 3. Staining for KIR molecules was performed using a combination of two clones for the antibody, 180704 and HP-MA4, as each recognizes a distinct subset of KIR molecules. Dead cells were excluded by light scatter profile and 7-AAD or DRAQ7 staining.

Figure 5:
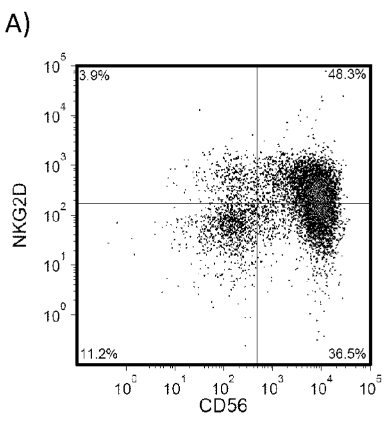
FIG. 5 shows the expression by differentiated $CD56^+$ NK cells of phenotypic markers associated with more mature NK cells. Cells were analyzed by flow cytometry for the expression of (A) NKG2D, (B) CD16, (C) CD94, (D) KIR, and (E) intracellular IFNγ. The histogram in (E) shows an overlay of gated $CD56^+$ NK cells stimulated with PMA/Ionomycin (black empty histogram) and unstimulated $CD56^+$ NK cells (solid grey histogram).
Figure 5:
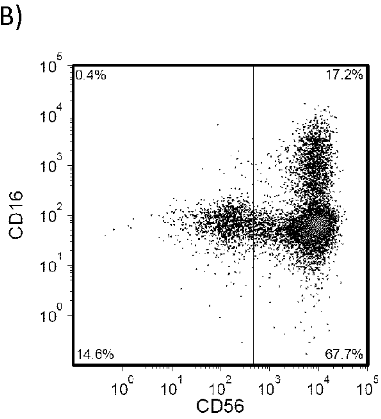
Figure 5:
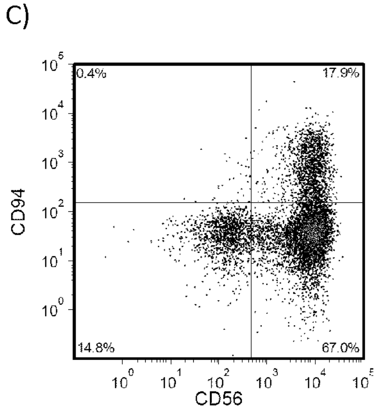
Figure 5:
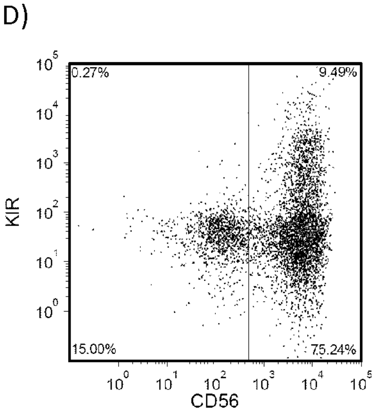
Figure 5:
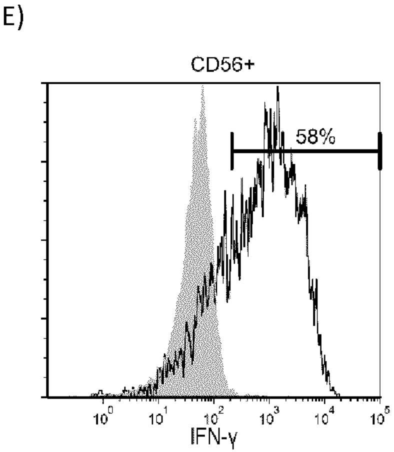

The results show that: approximately 50% of analyzed cells co-express CD56 and NKG2D (FIG. 5A); approximately 17% of analyzed cells co-express CD56 and CD16 (FIG. 5*b*); approximately 18% of analyzed cells co-express CD56 and CD94 (FIG. 5*c*); and approximately 10% of analyzed cells co-express CD56 and KIR (FIG. 5*d*).

Production of IFNγ by the differentiated $CD56^+$ NK cells was also measured. For IFNγ intracellular staining, differentiated $CD56^+$ NK Cells were stimulated with PMA/Ionomycin for 2 hours. Brefeldin A was added and the cells were incubated for another 2 hours. The cells were harvested and stained for CD56 and Zombie NIR viability dye then fixed, permeabilized and stained for intracellular IFNγ. The results in FIG. 5E show that approximately 58% of the differentiated $CD56^+$ NK cells express intracellular IFNγ upon stimulation.

Example 5: Lack of Expression of T Cell Markers on Differentiated Cells $CD56^+$ NK cells were differentiated as described in Examples 1 and 2 in the presence of pyrimidoindole compounds and analyzed on day 28 by flow cytometry for the expression of a T cell marker. The analyzed cells were stained for CD3 essentially as described in Example 3. Dead cells were excluded by light scatter profile and 7-AAD or DRAQ7 staining.

Figure 6:
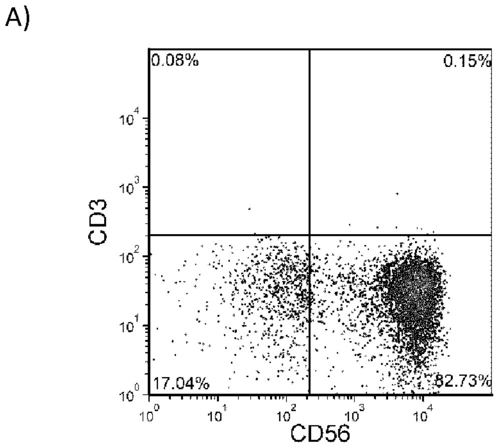
FIG. 6 shows that differentiated $CD56^+$ NK cells do not express a T cell marker. (A) NK cell progenitors of a first donor cultured in the presence of UM171 do not express CD3. (B) NK cell progenitors of a second donor cultured in the presence of UM171 do not express CD3. (C) NK cell progenitors of a second donor cultured in the presence of UM729 do not express CD3.
Figure 6:
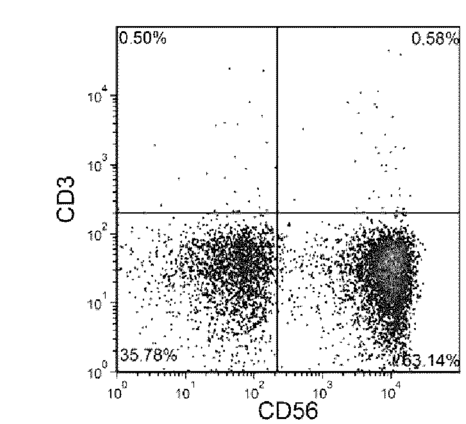
Figure 6:
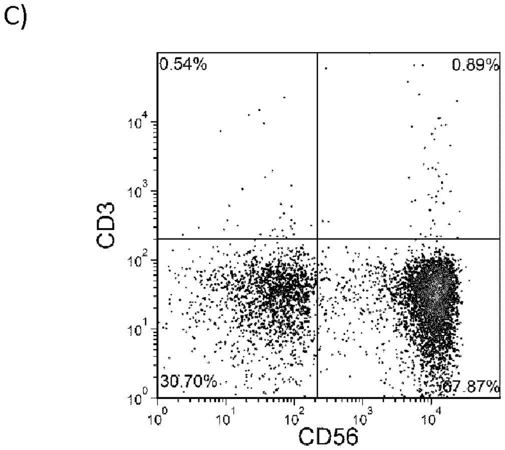

The expression of CD3 is virtually absent among the cells differentiated from a cord blood sample of a first donor, cultured in the presence of 100 nM UM171 (FIG. 6A). Similarly, the expression of CD3 is virtually absent among the cells differentiated from a cord blood sample of a second donor, cultured in the presence of 100 nM UM171 (FIG. 6B) or 1 μM UM729 (FIG. 6C).

These results suggest that the differentiated $CD56^+$ cells are not T cells or NKT cells.

Example 6: Differentiated $CD56^+$ NK Cells are Cytotoxic $CD56^+$ NK cells were differentiated as described in Examples 1 and 2 in the presence of 1 μM UM729 and analyzed on day 28 for their cytotoxicity toward K562 target cells.

For the cytotoxicity assay, the in vitro generated $CD56^+$ NK cells were co-cultured with Calcein AM labeled K562 cells for 4 hours at a ratio of 5:1 for effector cells (NK cells) to target cells (K562 cells), and supernatants were analysed for the release of fluorescent Calcein from killed target cells.

Peripheral blood (PB) NK cells and Monocytes isolated using EasySep™ (STEMCELL Technologies, Catalogue #17955 and 19359, respectively) were also co-cultured with labelled K562 cells as positive and negative controls, respectively, at the same ratios described above. PB NK cells were cultured overnight in the medium of Example 2, except that it did not include pyrimidoindole compounds while PB monocytes were cultured overnight in StemSpan™ SFEM II only.

To detect spontaneous release of calcein, control wells containing only calcein AM-labeled K562 target cells were set up. The labeled K562 cells were treated with 1% Triton™ X-100 to measure maximum release. After incubation, plates were centrifuged at 500×g for 5 minutes and 100 μL of supernatant was transferred to black plates and analyzed using a SpectraMax® microplate reader (excitation 485 nm/emission 530 nm). Results are expressed as % specific lysis: [(test release−spontaneous release)×100]/(maximum release−spontaneous release).

Figure 7:
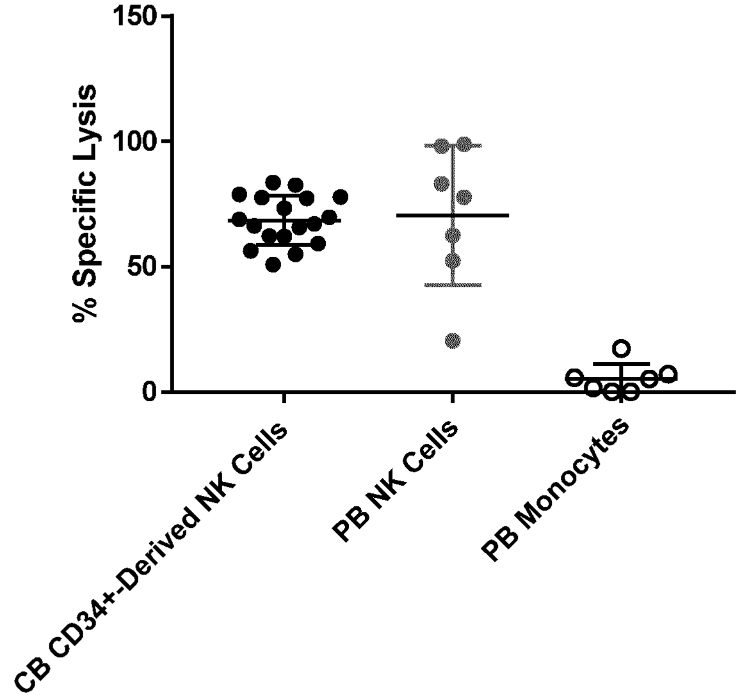
FIG. 7 shows that differentiated $CD56^+$ NK cells are cytotoxic. Peripheral blood (PB) NK cells and Monocytes were also co-cultured with calcein AM labelled K562 cells at an effector to target ratio of 5:1 as positive and negative controls, respectively. Results are expressed as % specific lysis of K562 cells: [(test release−spontaneous release)×100]/(maximum release−spontaneous release). Shown are means±SD (CB $CD34^+$-derived NK cells: n=18, PB NK cells and monocytes: n=7).

FIG. 7 shows that the NK cells differentiated as described herein are able to kill K562 target cells and their killing ability is similar to that of NK cells isolated from peripheral blood of adult donors.

Example 7: The Effects of Pyrimidoindole Compounds are Specific to NK Cell Progenitors $CD4^+$ CB cells were isolated and cultured as described in Example 1. As in Example 1 and 2 the different media were used in the day 0-14 and the day 14-28 cultures, except the day 0-14 culture medium was further supplemented with 100 nM UM171 to investigate its effect on the differentiation of $CD4^+$ HSPC to NK cells.

In these experiments UM171 was added to the cultures at different time points: days 0-14 (+/−); days 14-28 (−/+); or days 0-28 (+/+). Cultures without UM171 were also set up (−/−). Cells were either analyzed at day 28 for CD56 expression (FIG. 8) or at day 14 for CD7 and CD5 expression (FIG. 9).

Cultures exposed to UM171 between days 14-28 (−/+) experienced an increase in NK cell frequency and yield when compared to cultures lacking UM171 on these days (−/−), and cultures exposed to UM171 between days 0-14 (+/−) resulted in lower $CD56^+$ cell frequency and yield as compared to cultures lacking UM171 on days 0-14 (−/−) (FIGS. 8A and 8B). The (+/+) condition indicates that the inclusion of UM171 during days 14-28 can compensate for the effects of this compound on day 0-14 cultures.

FIGS. 9A and 9B show the results of culturing $CD34^+$ HSPC in the day 0-14 culture media further supplemented with UM171. At day 14, a clear reduction in the frequency and yield of $CD7^+CD5^+$ NK cell progenitors was observed as compared to cultures not supplemented with UM171 during days 0-14 (FIGS. 9A and 9B).

Figure 8:
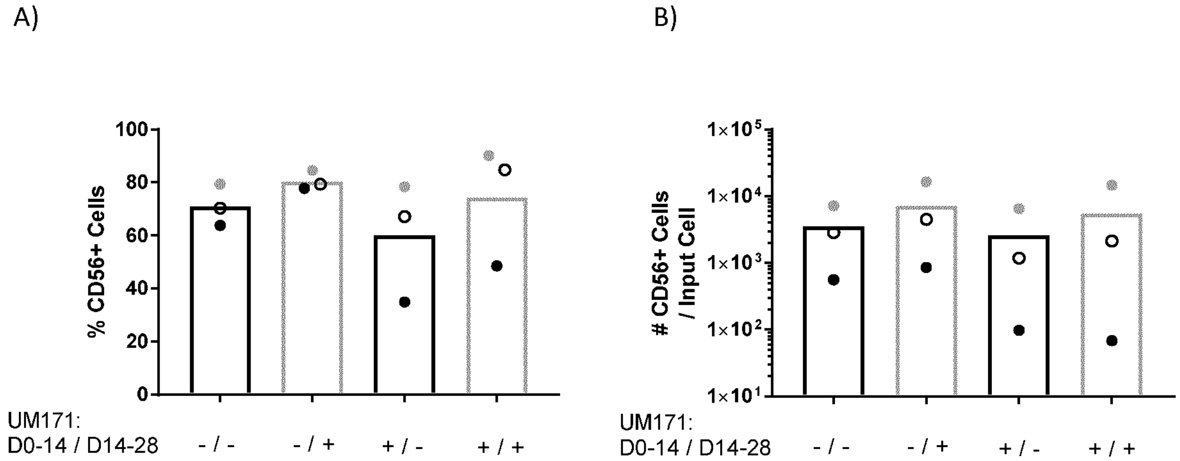
FIG. 8 shows that pyrimidoindole compounds specifically affect NK cell progenitors and not $CD34^+$ HSPCs. Cord blood-derived $CD34^+$ HSPC cells were plated on day 0, and UM171 was added to NK differentiation cultures at different times: days 0-14 (+/−); days 14-28 (−/+); or days 0-28 (+/+). Cultures without UM171 were also established: days 0-28 (−/−). The effect of UM171 addition on differentiation of NK cells was assessed in terms of (A) frequency of $CD56^+$ NK cells and (B) yield of $CD56^+$ NK cells per input cell (i.e. day 0 cells).
Figure 9:
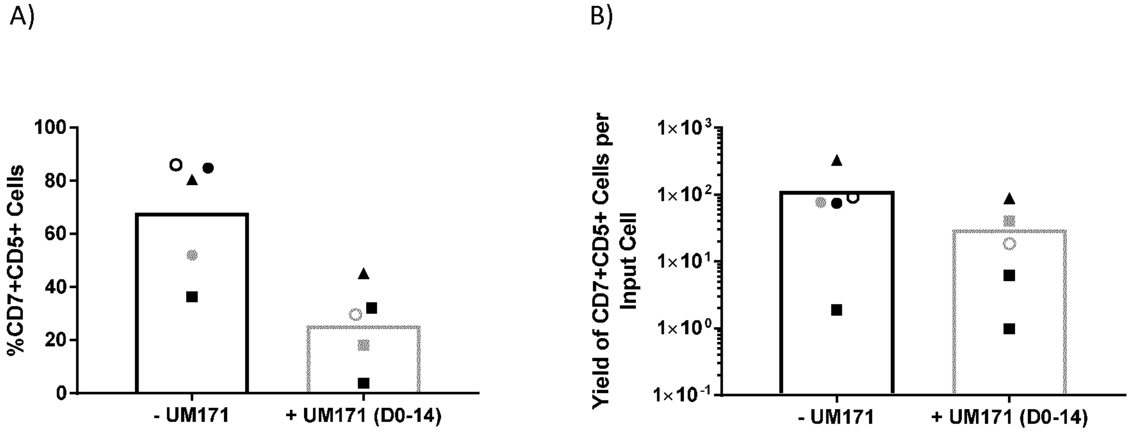
FIG. 9 shows that pyrimidoindole compounds inhibit the differentiation of $CD34^+$ HSPCs into NK cell progenitors. $CD7^+CD5^+$ cells were analyzed on day 14 of NK cell differentiation cultures after having been cultured in the presence or absence of UM171. The effect of UM171 addition on differentiation of $CD34^+$ cells into NK cell progenitors was assessed in terms of (A) frequency of $CD7^+CD5^+$ NK cell progenitors and (B) yield of $CD7^+CD5^+$ NK progenitor cells per input cell.

Together, these data demonstrate that UM171 does not promote (and may actually inhibit) the generation of NK cell progenitors from $CD34^+$ HSPC (FIGS. 8 and 9), but does promote the differentiation of NK cell progenitors into NK cells (FIG. 8)

Example 8: Characterizing the Phenotype of NK Cell Progenitors $CD34^+$ CB cells were isolated and cultured as described in Example 1 up to the day 14 time point. NK cell progenitors derived from CB $CD34^+$ HSPCs after 14 days of culture were stained, essentially as described in Example 3, with antibodies against markers CD5, CD7, and CD56. $CD56^-$ cells were gated and $CD7^+CD5^-$, $CD7^+CD5^+$, $CD5^-CD7^-$ cells were sorted using a BD FACSAria Fusion fluorescence-activated cell sorter.

Figure 10:
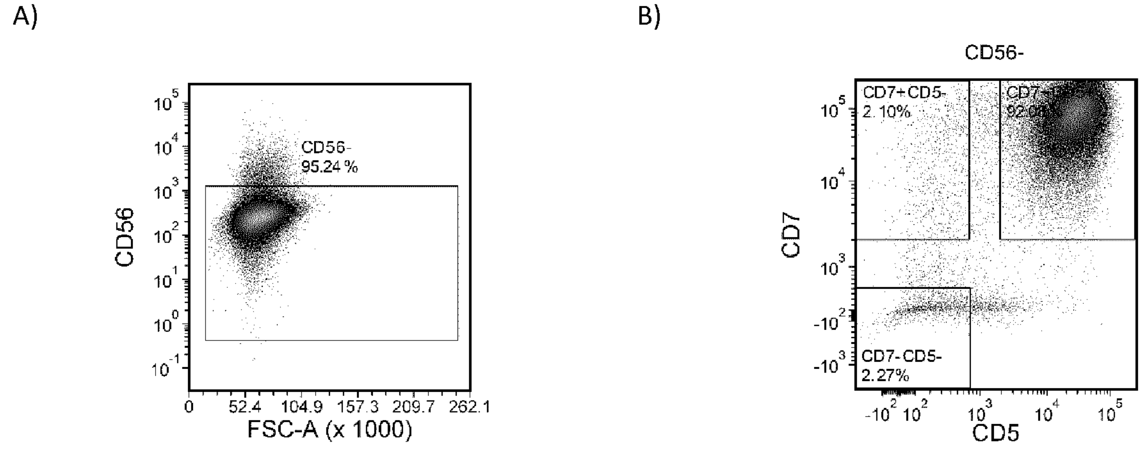
FIG. 10 shows the phenotypes of an intermediate population of cells differentiated from $CD34^+$ HSPCs after 14 days of culture. (A) Cells were analyzed by flow cytometry for the expression of CD56. (B) $CD56^-$ cells were analyzed by flow cytometry for the expression or absence of expression of NK cell progenitor markers CD7 and CD5.

After two weeks of culture, the majority of cells differentiated from CB $CD34^+$ cells are $CD56^-$ (FIG. 10A), and these cells comprise a heterogeneous population essentially composed of $CD7^+CD5^-$, $CD7^+CD5^+$ and $CD7^-CD5^-$ cells.

To investigate which subset of the day 14 population of NK cell progenitors is targeted by pyrimidoindole compounds, the $CD7^+CD5^-$, $CD7^+CD5^+$ and $CD7^-CD5^-$ sorted populations were each cultured for another 14 days in NK Cell Differentiation medium without or with UM729.

Figure 11:
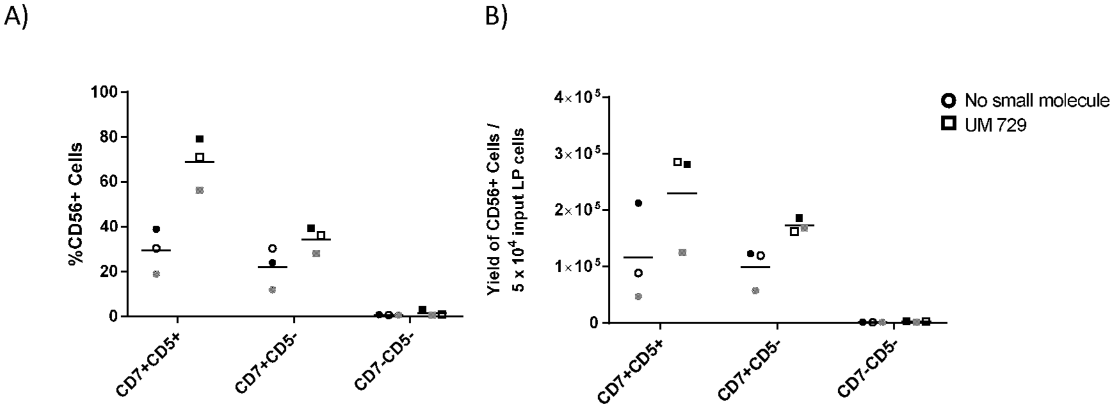
FIG. 11 shows that pyrimidoindole compounds promote the differentiation of $CD7^+CD5^+$ and $CD7^-CD5^-$ NK cell progenitors to NK cells. Each population of cells in FIG. 10(B)—$CD7^+CD5^+$, $CD7^+CD5^-$, $CD7^-CD5^-$—was sorted by flow cytometry and cultured in NK cell differentiation medium in the presence (square data points) or absence (circle data points) of UM729. The effect of UM729 addition on the differentiation of NK cells was assessed in terms of (A) frequency of $CD56^+$ NK cells and (B) yield of $CD56^+$ NK cells per input progenitor cells (i.e. sorted day 14 cells). Horizontal bars are mean of three donors; each donor is represented by a differently shaded symbol.

The results show that $CD7^+CD5^+$ and $CD7^+CD5^-$ cells respond to UM729 and differentiate to NK cells with higher frequency (FIG. 11A) and yield (FIG. 11B) as compared to culture conditions lacking UM729. $CD7^-CD5^-$ cells did not expand and differentiate to NK cells in either the presence or absence of UM729. $CD7^+CD5^+$ cells generated higher frequency and yield of NK cells compared to $CD7^+CD5^-$ cells in the presence of UM729, and thus this population appears to be the main population of NK cell progenitors that differentiate to $CD56^+$ NK cells in response to UM729 (FIG. 11).

Example 9: Aryl Hydrocarbon Receptor Antagonist Negatively Impacts Differentiation of NK Cells Compounds other than pyrimidoindole compounds, such as aryl hydrocarbon receptor (AhR) antagonist, are reported to expand HSPCs in culture. Thus, the effect of an AhR antagonist on differentiation of NK cell progenitors was also tested $CD34^+$ CB cells were isolated and cultured as described in Example 1 up to the day 14 time point. Day 14 NK cell progenitors were further cultured in NK Cell Differentiation medium, essentially as described in Example 1, except in the absence of an added pyrimidoindole compound but in the presence or absence of 5 μM CH223191.

Figure 12:
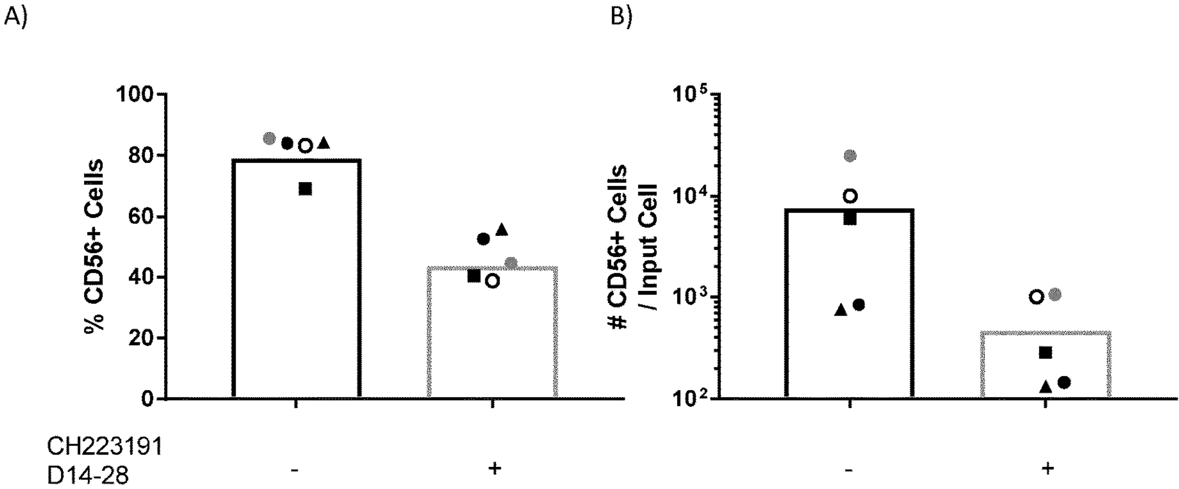
FIG. 12 shows that the effects of pyrimidoindole compounds on the differentiation of NK cells are not recapitulated using an aryl hydrocarbon receptor (AhR) antagonist. NK cell progenitors were cultured in either the presence or absence of 5 μM CH223191. The effect of CH223191 addition on the differentiation of NK cells was assessed in terms of (A) frequency of $CD56^+$ NK cells and (B) yield of $CD56^+$ NK cells per input cell (i.e. day 0 cells).

The data show that addition of CH223191 to differentiation cultures of NK cell progenitors results in decreased $CD56^+$ NK cell frequency (FIG. 12A) and yield (FIG. 12B). This suggests that the observed effects on the differentiation of NK cell progenitors to NK cells are specific to pyrimidoindole compounds and not to AhR antagonists.

Example 10: $CD34^+$ Cell NK Progenitors do not Respond to Pyrimidoindole Compounds $CD34^+$ CB cells were isolated and cultured as described in Example 1 up to the day 14 time point. NK cell progenitors derived from CB $CD34^+$ HSPCs after 14 days of culture were stained, essentially as described in Example 3, with antibodies against markers CD5, CD7, CD34, and CD56. $CD56^-$ cells were gated and $CD34^+CD7^+CD5^+$ and $CD34^+$ $CD7^+CD5^+$, and $CD34^-$ $CD7^+CD5^-$ and $CD34^-CD7^+CD5^+$ were sorted using a BD FACSAria Fusion fluorescence-activated cell sorter. CD7 cells were sorted as a negative control.

To investigate which subset of the day 14 population of NK cell progenitors is targeted by pyrimidoindole compounds, the $CD34^+CD7^+CD5^-$ and $CD34^+CD7^+CD5^+$, and $CD34^-CD7^+CD5^-$ and $CD34^-$ $CD7^+CD5^+$ sorted populations were each cultured for another 14 days in NK Cell Differentiation medium with or without UM729.

Figure 13:
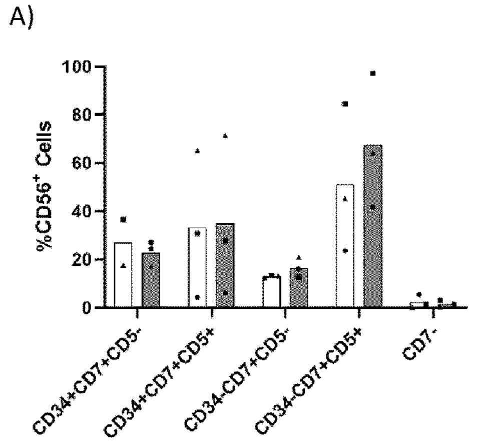
FIG. 13 shows that pyrimidoindole compounds preferentially affect $CD34^-$ subsets of NK cell progenitors. Sorted day 14 populations of NK cell progenitors were plated in the presence (grey bars) or absence (white bars) of UM729 and cultured for 14 days. The effect of UM729 addition on differentiation of NK cells was assessed in terms of (A) frequency of $CD56^+$ NK cells and (B) yield of $CD56^+$ NK cells per input progenitor cells. Each dot represents an individual cord blood donor.
Figure 13:
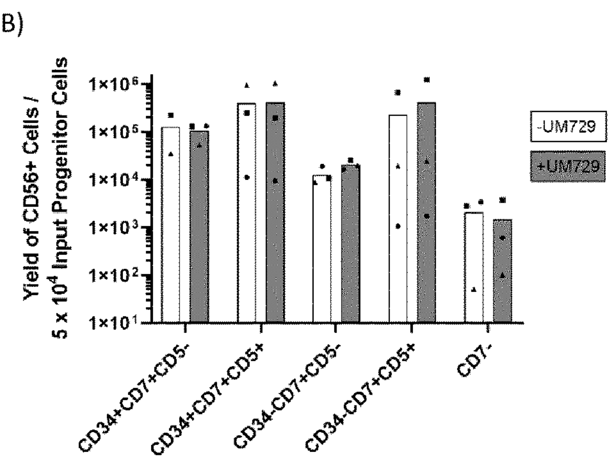

The results show that only $CD34^-CD7^+CD5^-$ and $CD34^-$ $CD7^+CD5^+$ cells respond to UM729 and differentiate to NK cells with higher frequency (FIG. 13A) and yield (FIG. 13B) as compared to culture conditions lacking UM729. Therefore, the more immature $CD34^+$ NK progenitor cell subsets do not appear responsive to the effect(s) of UM729.

Example 11: Effects of Pyrimidoindole Compounds on Differentiating NK Cells from PSC Three induced pluripotent stem cell (iPSC) lines—WLS-1C, STiPSC M001, and STiPS F016—and one embryonic stem cell (ESC) line—H1 were maintained in mTeSR™ 1. The PSC were harvested and dissociated using accutase into single cell suspensions and were filtered using 37 μm reversible strainer (STEMCELL Technologies).

Single cell suspensions of PSC were seeded into AggreWell plates (STEMCELL Technologies) to form 500- cell aggregates. The seeded cells were cultured in a mesoderm differentiation medium and 10 μM Y027632 (STEMCELL Technologies). After 3 days (i.e. on day 3) in culture the medium was changed to induce hematopoietic lineage differentiation. After 7 days (i.e. on day 10) in culture the aggregates were harvested and dissociated using collagenase II and a trypsin-containing solution.

Dissociated cells were enriched for $CD34^+$ cells using EasySep™ Human CD34 Positive Selection Kit II (STEMCELL Technologies, catalogue #17856). To differentiate the $CD34^+$ cells into NK cell progenitors, enriched $CD34^+$ cells were plated at $5\times10^4$ cells/mL in StemSpan™ SFEM II medium (STEMCELL Technologies) supplemented with StemSpan™ Lymphoid Progenitor Expansion Supplement (STEMCELL Technologies) onto plates coated with StemSpan™ Lymphoid Differentiation Coating Material (STEMCELL Technologies) and cultured for 14-days. Half-medium changes were performed every 3-4 days.

After 14-days in culture, the population of NK cell progenitors were re-plated at $1\times10^5$ cells/mL onto uncoated plates in NK Cell Differentiation Medium either in the presence or absence of UM729 and cultured for 14-more days.

Figure 14:
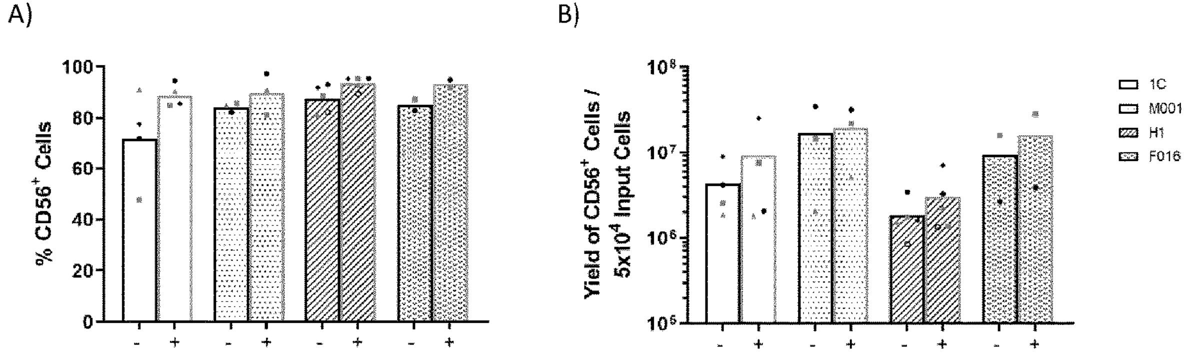
FIG. 14 shows that populations of NK cell progenitors derived from four PSC lines, 1C, M001, H1 and F016, respond to pyrimidoindole compounds. PSC-derived $CD34^+$ cells differentiated to a population of NK cell progenitors were plated in the absence (−) or presence (+) of UM729 and cultured for 14 days. The effect of UM729 addition on differentiation of PSC-derived NK cells was assessed in terms of (A) frequency of $CD56^+$ PSC-derived NK cells and (B) yield of $CD56^+$ PSC-derived NK cells per input $CD34^+$ cells. Each dot represents an individual biological replicate.

The cells were stained for CD56 essentially as described in Example 3 and analyzed for frequency of $CD56^+$ cells and yield of $CD56^+$ cells per $5\times10^4$ input PSC-derived $CD34^+$ cells. Both the frequency (FIG. 14A) and yield (FIG. 14B) of $CD56^+$ cells increased after culturing the PSC-derived population NK cell progenitors in the presence of UM729, as compared to culturing such cells in the absence of UM729. Therefore, the presence of UM729 during days 24 to 38 of culturing PSC-derived NK cell progenitors increases the frequency and yield of $CD56^+$ cells.

Example 12: Pyrimidoindole Compounds Inhibit the Differentiation of PSC-Derived $CD34^+$ Cells Into NK Cell Progenitors PSC-derived $CD4^+$ cells were generated as described in Example 11. The PSC-derived $CD4^+$ cells were cultured as described in Example 11, except the effect of the presence or absence of 1 μM UM729 on the differentiation of a population of NK cell progenitors was assessed.

Figure 15:
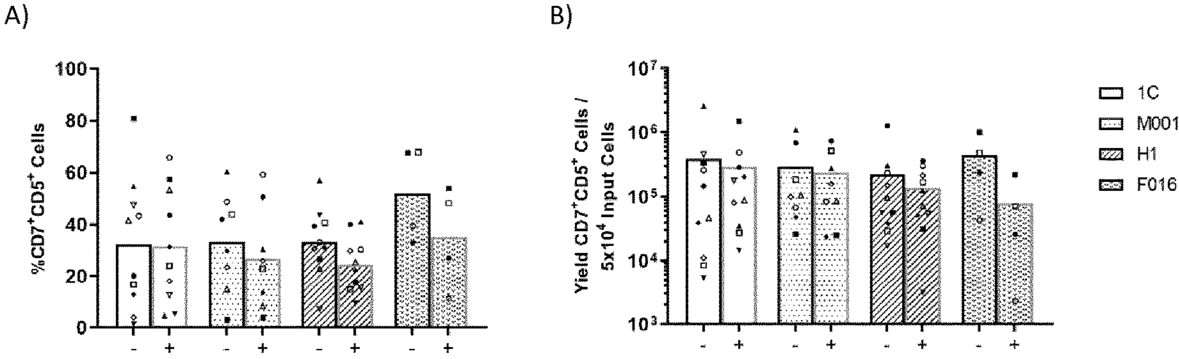
FIG. 15 shows that pyrimidoindole compounds have a negative effect on the differentiation of populations of NK cell progenitors from PSC-derived $CD34^+$ cells. $CD34^+$ cells derived from four PSC lines, 1C, M001, H1 and F016 were plated in the absence (−) or presence (+) of UM729 and cultured for 14 days. The effect of UM729 addition on differentiation of PSC-derived $CD34^+$ cells to populations of PSC-derived NK cell progenitors was assessed in terms of (A) frequency of $CD5^+CD7^+$ PSC-derived NK cell progenitors and (B) yield of $CD5^+CD7^+$ PSC-derived NK cell progenitors per input cells. Each dot represents an individual biological replicate.

The cells were stained for CD5 and CD7 essentially as described in Example 3 and analyzed for frequency of $CD5^+CD7^+$ cells and yield of $CD5^+CD7^+$ cells per $5\times10^4$ input PSC-derived $CD4^+$ cells. Both the frequency (FIG. 15A) and yield (FIG. 15B) of $CD5^+CD7^+$ cells decreased after culturing the PSC-derived $CD4^+$ cells in the presence of UM729, as compared to culturing such cells in the absence of UM729. Therefore, the presence of UM729 during days 10 to 24 of culturing PSC-derived $CD4^+$ cells decreases the frequency and yield of $CD5^+CD7^+$ NK progenitor cells.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

The invention claimed is:

1. A method for differentiating NK cells, comprising:

providing a population of NK cell progenitors, wherein the population of NK cell progenitors arise in contact with a NK cell progenitor differentiation medium and a stroma cell replacement comprising components selected from fibronectin, whether full-length or a fragment thereof, VCAM-1, and an immobilized Notch ligand; and contacting the population of NK cell progenitors in culture with an NK cell differentiation medium comprising a basal medium, IL-15 and a pyrimidoindole compound at a concentration between 10 nM and 3 μM and for a time sufficient to yield NK cells, wherein the NK cells co-express i) CD56, NKG2D and NKp44, or ii) CD56, NKG2D and NKp30, wherein an increased frequency and/or yield of NK cells co-expressing i) CD56, NKG2D and NKp44, or ii) CD56, NKG2D and NKp30 is obtained when contacting the population of NK cell progenitors with the NK cell differentiation medium as compared to when the NK cells are differentiated from the population of NK cell progenitors in a NK cell differentiation medium devoid of an added pyrimidoindole compound, and wherein the NK cells produce intracellular interferon γ upon stimulation.

2. The method according to claim 1, wherein the population of NK cell progenitors express CD7 or CD5, or both.

3. The method according to claim 1, wherein the NK cells increase in frequency during the contacting step or increase in number during the contacting step, or both.

4. The method according to claim 1, wherein the population of NK cell progenitors increase or decrease in frequency or number during the contacting step.

5. The method according to claim 1, wherein the providing and contacting steps are not in the presence of stromal cells or a stroma cell replacement.

6. The method according to claim 1, wherein the providing and contacting steps are not in the presence of an aryl hydrocarbon receptor antagonist.

7. The method according to claim 1, wherein the time is at least 1 week or about 2 weeks.

8. The method according to claim 1, wherein the NK cells are cytotoxic.

9. The method according to claim 1, wherein the population of NK cell progenitors is derived or isolated from a primary sample.

10. The method according to claim 1, wherein the population of NK cells is differentiated from a pluripotent stem cell.

11. The method of claim 1, wherein less than 5% of the NK cells express CD3.

12. A method for differentiating NK cells, comprising:

providing a population of NK cell progenitors, wherein the population of NK cell progenitors arise in contact with a NK cell progenitor differentiation medium and a stroma cell replacement comprising components selected from fibronectin, whether full-length or a fragment thereof, VCAM-1, and an immobilized Notch ligand; and contacting the population of NK cell progenitors in culture with an NK cell differentiation medium comprising a basal medium, IL-15 and a pyrimidoindole compound at a concentration between 10 nM and 3 μM and for a time sufficient to yield NK cells, wherein the NK cells co-express i) CD56, NKG2D and NKp44, or ii) CD56, NKG2D and NKp30, wherein an increased frequency and/or yield of NK cells co-expressing i) CD56, NKG2D and NKp44, or ii) CD56, NKG2D and NKp30 is obtained when contacting the population of NK cell progenitors with the NK cell differentiation medium as compared to when the NK cells are differentiated from the population of NK cell progenitors in an NK cell differentiation medium devoid of an added pyrimidoindole compound, wherein less than 5% of the NK cells express CD3, and wherein the NK cells produce intracellular interferon γ upon stimulation.

13. The method of claim 12, wherein the population of NK cell progenitors express CD7 or CD5, or both.

* * * * *